United States Patent [19]

Lemasters et al.

[11] Patent Number: 5,145,771
[45] Date of Patent: Sep. 8, 1992

[54] RINSE SOLUTION FOR ORGANS AND TISSUES

[75] Inventors: John J. Lemasters; Ronald G. Thurman, both of Chapel Hill, N.C.

[73] Assignee: The University of North Carolina at Chapel Hill, Chapel Hill, N.C.

[21] Appl. No.: 596,115

[22] Filed: Oct. 10, 1990

Related U.S. Application Data

[63] Continuation-in-part of Ser. No. 509,061, Apr. 12, 1990, abandoned.

[51] Int. Cl.$^5$ .......................... A01N 1/02; A61K 37/02
[52] U.S. Cl. ........................................ 435/1; 530/331; 544/277
[58] Field of Search ...................... 514/2, 60, 3; 435/1; 530/331; 544/277

[56] References Cited

U.S. PATENT DOCUMENTS

| | | | |
|---|---|---|---|
| 4,798,824 | 1/1979 | Belzer et al. | 514/60 |
| 4,873,230 | 10/1989 | Belzer et al. | 514/60 |
| 4,879,283 | 11/1989 | Belzer et al. | 514/60 |
| 4,920,044 | 4/1990 | Bretan, Jr. | 435/1 |

OTHER PUBLICATIONS

Beyersdorf, "Reperfusion Solution for Peripheral Ischemia" Chem Abstracts 113: 84849w (1990).
Anundi et al. Res. Commun. Chem. Path. Pharm. 55(1) 111–116 (1987).
Belzer and Southard, "Transplantation" vol. 45 (1988) 673–676.
D. Adkison et al., Acta Physiol. Scand. Supp. 548, 101–107 (1986).
I. Anundi et al., Am. J. Physiol. 253, G390–G396 (1987).
G. Bellomo and S. Orrenius, Hepatology 5, No. 5, 876–882 (1985).
J. Bonventre and J. Cheung, Am. J. Physiol. 249, C149–C159 (1985).
J. Caldwell-Kenkel et al., Hepatology 10, No. 3, 292–299 (1989).
J. Caldwell-Kenkel et al., Transplantation 45, No. 4, 834–837 (1988).
P. Cobbold et al., Basic Res. Cardiol. 80 (Suppl. 2), 155–158 (1985).
K. Cowper et al., Biochem J. 266, 141–147 (1990).
R. Currin et al., FASEB J. 3, A626 (Abstract) (1989).
C. Ganote and J. Kaltenbach, J. Molec. Cell. Cardiol. 11, 389–406 (1979).
G. Gores et al., J. Clin. Invest. 83, 386–396 (1989).
G. Gores et al., Am. J. Physiol. 255, C315–C322 (1988).
N. Kamada and R. Calne, Transplantation 28, No. 1, 47–50 (1979).
R. Kloner et al., Am. J. Pathol. 74, No. 3, 399–413 (1974).
J. Lemasters et al., Cells of the Hepatic Sinusoid, vol. 2, E. Wisse, D. L. Knook and K. Decker, Eds., Kupffer Cell Foundation, Rijswijk, The Netherlands, pp. 277–280 (1989).
I. Marzi et al., Transplantation 48, No. 3, 463–468 (1989).
J. McCord, New Engl. J. Med. 312, No. 3, 159–164 (1985).
W. Rouslin and J. Erickson, J. Mol. Cell Cardiol. 18, 1187–1195 (1986).
P. Simpson and B. Lucchesi, J. Lab. Clin. Med. 110, No. 1, 13–30 (1987).
Y. Takei et al., Optical Microscopy for Biology, B. Herman and K. A. Jacobson, Eds., Alan R. Lisa, New York, pp. 487–498 (1990).
P. Bretan, Intracellular Flush Solution for Preserving Organs, U.S. Pat. No. 4,920,044.

Primary Examiner—Lester L. Lee
Assistant Examiner—B. Celsa
Attorney, Agent, or Firm—Bell, Seltzer, Park & Gibson

[57] ABSTRACT

Disclosed is a rinse for preservation solution for organs and tissues selected for transplantation. The solution can be used at all temperatures from 0° C. to normal body temperature and continues to be protective above 10° C. Methods for preparing organs and tissues preserved in a preservation solution prior to transplant into a recipient are also disclosed.

31 Claims, 10 Drawing Sheets

RINSE SOLUTION FOR ORGANS AND TISSUES

This invention was supported, in part, by NIH grant DK-37034. The government may have certain rights to this invention.

RELATED APPLICATIONS

This application is a continuation-in-part of copending U.S. patent application Ser. No. 07/509,061, filed Apr. 12, 1990, abandoned Oct. 17, 1991.

BACKGROUND OF THE INVENTION

The introduction of cyclosporine for immunosuppression during the 1980's revived interest in transplanting organs and tissues, specifically, the liver, pancreas, heart, lung and heart-lung. However, preservation methods that are successful for kidneys have proven unsuccessful for these other organs. Until recently, the clinical preservation of the heart, liver and pancreas was kept to a minimum and to no longer than six to ten hours. These organs are more complex to transplant than kidneys, and invariably the operations are performed during the night when operating rooms are available in the donor hospitals. Short preservation times for heart and liver also necessitate two surgical teams, one for the donor and another for the recipient. Extending preservation time for these organs to thirty hours would have the same impact on their transplantation as it did on kidney transplantation, namely, increasing organ availability, decreasing organ wastage, increasing organ sharing, and reducing costs.

A preservation solution useful for all donor organs, both for in situ organ cooling in the donor and for cold storage after the organ is harvested is available from E. I. du Pont de Nemours and Co. under the trademark VIASPAN TM and disclosed in U.S. Pat. No. 4,879,283. Solution for the Preservation of Organs, issued Nov. 7, 1989, U.S. Pat. No. 4,873,230, Composition for the Preservation of Organs, issued Oct. 10, 1989, and U.S. Pat. No. 4,798,824, Perfusate for the Preservation of Organs, issued Jan. 17, 1989, discloses a hydroxyethyl starch composition useful in the preservation solution disclosed in U.S. Pat. No. 4,879,283. The solution of U.S. Pat. No. 4,879,283 has greatly extended the preservation time of organs intended for transplantation, extending the viability of livers, for example, from six to ten hours to over twenty-four hours. This has allowed sufficient time for compatibility testing of the donor and recipient, increased organ availability, decreased organ wastage, and aided in reducing the cost of a transplant. Current practice is to rinse such preservation solutions from the organ with a Ringer's solution prior to transplanting the organ into a recipient. While the solution of U.S. Pat. No. 4,879,283 has been effective in extending the preservation time of organs intended for transplantation, cell injury still occurs. Therefore, a further reduction in cell injury and increased survival time is desirable.

An injury characterized by loss of endothelial cell viability occurs after cold ischemic storage of rat livers for eight or more hours in Euro-Collins solution or sixteen or more hours in Du Pont VIASPAN TM solution (Caldwell-Kenkel, J. C., R. G. Thurman and J. J. Lemasters (1988) *Transplantation* 45, 834–837; Caldwell-Kenkel, J. C., R. T. Currin, Y. Tanaka, R. G. Thurman and J. J. Lemasters (1989) *Hepatology* 10, 292–299). Lethal injury does not occur until after the stored organs are reperfused with warm physiologic buffer containing dissolved oxygen. Thus, endothelial cell killing after storage and reperfusion may properly be called a reperfusion injury. Loss of viability is specific for endothelial cells. Hepatic parenchymal cells, Kupffer cells and Ito cells retain viability under conditions where virtually all endothelial cells are nonviable. Moreover, parenchymal cell function remains intact by a number of criteria including oxygen uptake and carbohydrate metabolism (I. Marzi, Z. Zhong, J. J. Lemasters and R. G. Thurman (1989) *Transplantation* 48, 463–468).

Reperfusion injury after warm ischemia is a phenomenon which has been well documented in heart and other tissues including liver (R. A. Kloner, C. E. Ganote, D. A. Whalen and R. B. Jennings (1974) *Am. J. Pathol.* 74. 399–422: D. Adkison, M. E. Hollwarth, J. N. Benoit, D. A. Parks, J. M. MoCord and D. N. Granger (1986) *Acta Physiol. Scand. Suppl.* 548, 101–107). Proposed mechanisms to account for reperfusion injury include: formation of toxic oxygen species (e.g., superoxide, hydrogen peroxide and hydroxyl radical) (J. M. McCord (1985) *New Engl. J. Med.* 312, 159–164; P. J. Simpson and B. R. Luchesi (1987) *J. Lab. Clin. Med.* 110, 13–30), disruption of ion homeostasis (G. Bellomo and S. Orrenius (1985) *Hepatology* 876–882), disruption of volume regulation (C. H. Ganote and J. P. Kaltenbach (1979) *J. Molec. Cell. Cardiol.* 11, 389–406 (1979)), and mechanical trauma (P. H. Cobbold, P. K. Bourne and K. S. R. Cuthbertson (1985) *Basic Res. Cardiol.* 80 (Suppl. 2), 155–158). Although prevailing opinion is that acidosis is detrimental during ischemia and organ preservation (W. Rouslin and J. L. Erickson (1986) *J. Molec. Cell Cardiol.* 18, 1187–1195; F. O. Belzer and J. H. Southard (1988) *Transplantation* 45, 673–676), our studies indicate that the acidotic pH which occurs naturally during ischemia actually protects against hypoxic cell killing (J. V. Bonventre and J. Y. Cheung (1985) *Am. J. Physiol,* 249, C149–C159; G. J. Gores, A.-L. Nieminen, K. E. Fleishman, T. L. Dawson, B. Herman and J. J. Lemasters (1989) *Am. J. Physiol,* 255, C315–C322), an effect mediated by intracellular acidification (G. J. Gores, A.-L. Nieminen, B. E. Wray, B. Herman and J. J. Lemasters (1989) *J. Clin. Invest.* 83. 386–396). Rather, it is the abrupt return from acidotic to physiologic pH during reperfusion which may precipitate cell killing and contribute to reperfusion injury (R. T. Currin, G. J. Gores, R. G. Thurman and J. J. Lemasters (1989) FASEB J. A626; FASEB J., in press). Other factors which may also contribute to reperfusion injury in livers stored for transplantation surgery include activation of Kupffer cells (J. J. Lemasters, J. C. Caldwell-Kenkel, R. T. Currin, Y. Tanaka, I. Marzi and R. G. Thurman (1989) in Cells of the Hepatic Sinusoid, Vol. 2, E. Wisse, D. L. Knook and K. Decker, Eds., Kupffer Cell Foundation, Rijswijk, The Netherlands, pp. 277–280), disruption of the microcirculation (Y. Takei, I. Marzi, G. J. Gores, R. T. Currin, J. J. Lemasters and R. G. Thurman (1990) in Optical Microscopy for Biology, B. Herman and K. A. Jacobson, Eds., Alan R. Lisa, New York, pp. 487-98), and dysfunction of mitochondria (I. Anundi, J. King, D. A. Owen, H. Schneider, J. J. Lemasters and R. G. Thurman (1987) *Am. J. Physiol.* 253, G390–G396).

SUMMARY OF THE INVENTION

In accordance with the invention disclosed is a rinse or preservation solution for organs and tissues selected for transplantation. As a rinse solution, it is used to rinse organs which had been stored in various preservation or storage solutions just prior to completion of transplantation surgery.

The described rinse solution has been designed to counteract various mechanisms which have been hypothesized to cause reperfusion injury: extracellular inorganic ions to match the normal ionic content of blood, especially sodium and potassium concentration (115 mM NaCl, 5 mM KCl, 1.3 mM $CaCl_2$, 1 mM $KH_2PO_4$ and 1.2 mM $MgSO_4$), antioxidants against oxygen-based free radicals (1 mM allopurinol, 1 mM desferrioxamine, 3 mM glutathione), vasodilators to improve microcirculation (2 $\mu$M nicardipene, 1 mM adenosine), substrates to regenerate adenosine triphosphate (ATP) (10 mM fructose, 10 mM glucose plus 100 U/1 insulin), mildly acidic pH (20 mM 3-(N-morpholino)propane sulfonic acid ("Mops"), pH 6.5) to prevent the detrimental effects of an abrupt increase of pH after reperfusion and, optionally, but preferably, colloid oncotic support against interstitial edema (e.g., 50 g/1 modified hydroxyethyl Du Pont Pentastarch TM). These components are dissolved in water.

Another aspect of the present invention is a method of transplanting an organ into a recipient, the method comprising the steps of (a) maintaining the organ in an organ preservation solution; then (b) rinsing the organ with an organ transplant rinse solution, the organ transplant rinse solution having a pH of from about 6.0 to about 7.1; and then (c) transplanting the rinsed organ into the recipient. Preferably the organ preservation solution has a pH of not less than about 7.2.

Rinse solutions of the present invention are characterized by a physiological concentration of crystalloid ions, in contrast to currently preferred preservation solutions.

Adenosine, at certain concentrations, has been found to be particularly important to the beneficial effects of rinse solutions of the present invention. Accordingly, rinse solutions of the present invention may comprise extracellular inorganic ions to match the normal ionic content of blood, especially sodium and potassium concentration, and adenosine at a concentration of from about 0.12 mM to about 1.2 mM. Such a solution may optionally contain other ingredients for a rinse solution as specified herein, such as at least one antioxidant in an amount effective to inhibit the generation of reactive oxygen species.

DETAILED DESCRIPTION OF THE INVENTION

Figure 1:
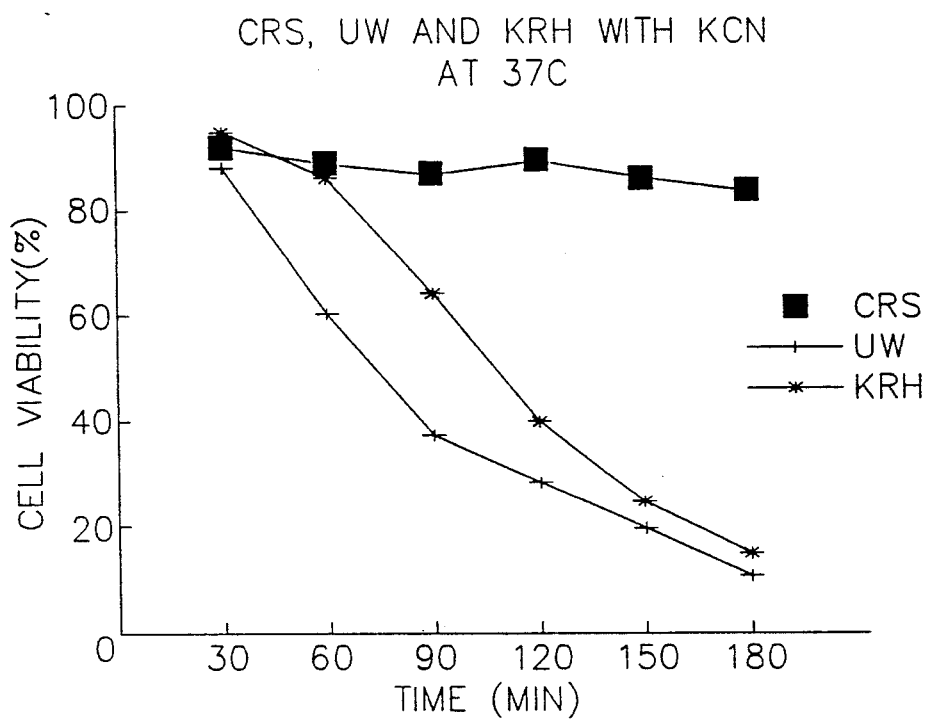
FIG. 1 shows the viability of isolated hepatocytes at 37° C. in various solutions.

Suitable organs and tissues for practicing the present invention are, for example, liver, pancreas, kidney, lung, heart, heart valves, arteries and veins, vascular segments, ligaments and tendons, cellular components from liver and pancreas, or of blood and bone marrow. Liver is particularly preferred. Suitable recipients for practicing the invention include mammalian recipients, including both human and animal (e.g., dog, cat, horse) recipients. The solution can be used at all temperatures, from 0° C. to normal body temperature, 37° C., and not solely at lower temperatures. At temperatures of from about 12° C. to about 37° C., the solution is more protective than other known preservation solutions. Unlike other storage solutions, it continues to be protective above 10° C.

The described solution is intended for use in rinsing the preservation or storage solution from the organ or tissue prior to implantation. It can also be used as a preservation or storage solution and is not limited to cold storage, but can be used at all temperatures, from about 0° C. to normal body temperature. Likewise, the solution is intended for use in perfusing tissue in situ, for example, ischemic brain, heart, limbs or bowel, namely, an organ or tissue whose circulation is blocked by a blood clot. By rinsing the organ or tissue with the solution prior to blood reperfusion, reperfusion injury can be prevented or minimized. Rinsing may be carried out by any suitable means which brings the rinse solution in contact with the organ or tissue in place of the preservation solution, including immersion and perfusion.

The potassium concentration of the described rinse or preservation solution is maintained at a physiological level, less than about six milliequivalents per liter. It is desirable that a rinse solution not have a high potassium concentration. When used as a cardioplegic solution, the potassium concentration can be from about 15 to 25 milliequivalents per liter.

As one embodiment of the described invention, the rinse solution contains about 3 mM glutathione, 1 mM adenosine, 10 mM glucose, and sodium, potassium, calcium and magnesium ions, and a pH of 6.5. 2 µM of a calcium blocking agent such as nicardipene can be added. Other suitable blocking agents are nifedipine, diltiazem or verapamil. Fructose can replace the glucose. Ribose and adenine, together, can replace the adenosine. Preferably, the solution also contains about 5% hydroxyethyl starch, as described hereinafter.

Suitable antioxidants include, but are not limited to, allopurinol, desferrioxamine, glutathione, beta-carotene, catalase, superoxide dismutase, dimethyl thiourea, mannitol, and cyanidanol.

A suitable colloid is a modified hydroxyethyl starch having a weight average molecular weight of about 50,000 to one million daltons but a preferred hydroxyethyl starch is one having a molecular weight of from about 150,000 to about 350,000 daltons and degree of substitution of from about 0.4 to about 0.7. A more preferred colloid is hydroxyethyl starch having a weight average molecular weight of from about 200,000 to about 300,000 daltons. The preferred colloid is substantially free of hydroxyethyl starch having a molecular weight of less than about 50,000 daltons. In accordance with one embodiment of the present invention, the hydroxyethyl starch is dialyzed against distilled-deionized water or otherwise treated to remove several contaminants previously unknown to have an adverse affect on the effectiveness of hydroxyethyl starch preparations. The materials removed by the dialysis process are the very smallest hydroxyethyl starch components, including the ethylene glycol and ethylene chlorohydrin side products of the hydroxyethylation as well as the residual acetone and sodium chloride. Ethylene glycol and ethylene chlorohydrin are known to be toxic. Hence, their removal, even if present in small amount, is desirable. Other suitable, but less preferred, colloids are albumin, dextran, polyethylene glycol and polyvinyl pyrolidone.

In a preferred embodiment, the rinse or preservation solution composition includes, but is not limited to, the components in about the concentration ranges set forth in Table 1 below. As noted above, the hydroxyethyl starch is optional but preferred.

TABLE 1

| Concentration Ranges in 1 Liter | | | |
|---|---|---|---|
| 10% modified hydroxyethyl starch 30 g/L to 100 g/L | | | |
| NaCl | 85 mM | to | 145 mM |
| KCl | 3 mM | to | 6 mM |
| CaCl$_2$ | 1.0 mM | to | 1.6 mM |
| KH$_2$PO$_4$ | 0.7 mM | to | 1.3 mM |
| MgSO$_4$ | 0.9 mM | to | 1.5 mM |
| Allopurinol | 0.05 mM | to | 5.0 mM |
| Desferrioxamine | 0.02 mM | to | 2.0 mM |
| Glutathione | 0.5 mM | to | 10.0 mM |
| Nicardipene | 0.1 µM | to | 5.0 µM |
| Adenosine | 0.1 mM | to | 5.0 mM |
| Fructose | 1.0 mM | to | 50.0 mM |
| Glucose | 1.0 mM | to | 50.0 mM |
| Insulin | 5 U/L | to | 250 U/L |
| Mops | 2 mM | to | 40 mM |

As explained in connection with Example 5 below, the concentration of Adenosine preferably does not exceed about 2 mM.

One specific embodiment is prepared with the components in the amounts set forth in Table 2 below in accordance with the instructions set forth below.

TABLE 2

| Components of 1 Liter Rinse Solution | | |
|---|---|---|
| 500 mL | Distilled Deionized Water | |
| 50 g/L | 10% modified hydroxyethyl starch | |
| 115 mM | NaCl | 6.7 g |
| 5 mM | KCl | 0.37 g |
| 1.30 mM | CaCl$_2$ | 0.19 g |
| 1 mM | KH$_2$PO$_4$ | 0.14 g |
| 1.2 mM | MgSO$_4$ | 0.15 g |
| 1 mM | Allopurinol | 0.14 g |
| 1 mM | Desferrioxamine | 0.65 g |
| 3 mM | Glutathione | 0.92 g |
| 2 µM | Nicardipene | 0.80 mg |
| 1 mM | Adenosine | 0.32 g |
| 10 mM | Fructose | 1.8 g |
| 10 mM | Glucose | 1.8 g |
| 100 U/L | Insulin | 100 units |
| 20 mM | Mops | 4.2 g |

Using a 500 mL volumetric flask, measure 500 mL of 10% (weight/volume) hydroxyethyl starch solution and pour into a 1 L beaker. Add 400 mL of double distilled water and stir vigorously using a magnetic stir bar. Add the rest of the components one at a time. After all components are added, adjust the pH to 6.5 with 1–2 mL 5N NaOH. The solution should be stirred for at least thirty minutes. Transfer the solution to a 1 L volumetric flask and bring to 1 L final volume. Filter to remove any undissolved particles. After sterile filtration the solution is ready.

Still another embodiment is exemplified by Table 3 below. This embodiment takes into consideration the significance of adenosine, at proper concentration, in the present invention, as discussed in Example 5 below.

TABLE 3

| Concentration Ranges in 1 Liter | | | |
|---|---|---|---|
| NaCl | 85 mM | to | 145 mM |
| KCl | 3 mM | to | 6 mM |

TABLE 3-continued

| Concentration Ranges in 1 Liter | | | |
|---|---|---|---|
| CaCl$_2$ | 1.0 mM | to | 1.6 mM |
| KH$_2$PO$_4$ | 0.7 mM | to | 1.3 mM |
| MgSO$_4$ | 0.9 mM | to | 1.5 mM |
| Adenosine | 0.12 mM | to | 1.2 mM |

A composition according to Table 3 above may optionally include one, several, or all of the further ingredients specified in Table 1 above. Preferably, a composition according to Table 3 includes at least one antioxidant. Thus, one specific embodiment of a composition according to Table 3 is set forth in Table 4 below:

TABLE 4

| Components of 1 Liter Rinse Solution | | |
|---|---|---|
| 500 mL | Distilled Deionized Water | |
| 115 mM | NaCl | 6.7 g |
| 5 mM | KCl | 0.37 g |
| 1.30 mM | CaCl$_2$ | 0.19 g |
| 1 mM | KH$_2$PO$_4$ | 0.14 g |
| 1.2 mM | MgSO$_4$ | 0.15 g |
| 1 mM | Allopurinol | 0.14 g |
| 1 mM | Desferrioxamine | 0.65 g |
| 3 mM | Glutathione | 0.92 g |
| .12 mM | Adenosine | 0.038 g |

A composition according to Table 4 may be prepared in the same manner as set forth in connection with Table 2 above.

The following examples are intended to be illustrative of the present invention but should not be considered as limiting thereof.

EXAMPLE 1

Figure 2:
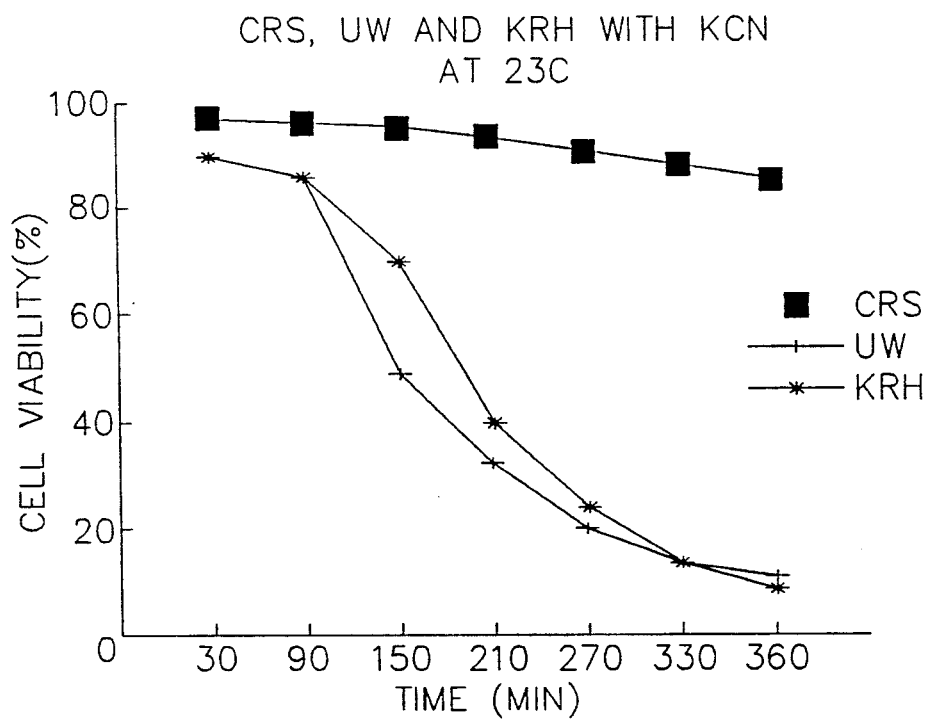
FIG. 2 shows the viability of isolated hepatocytes at 23° C. in various solutions.
Figure 3:
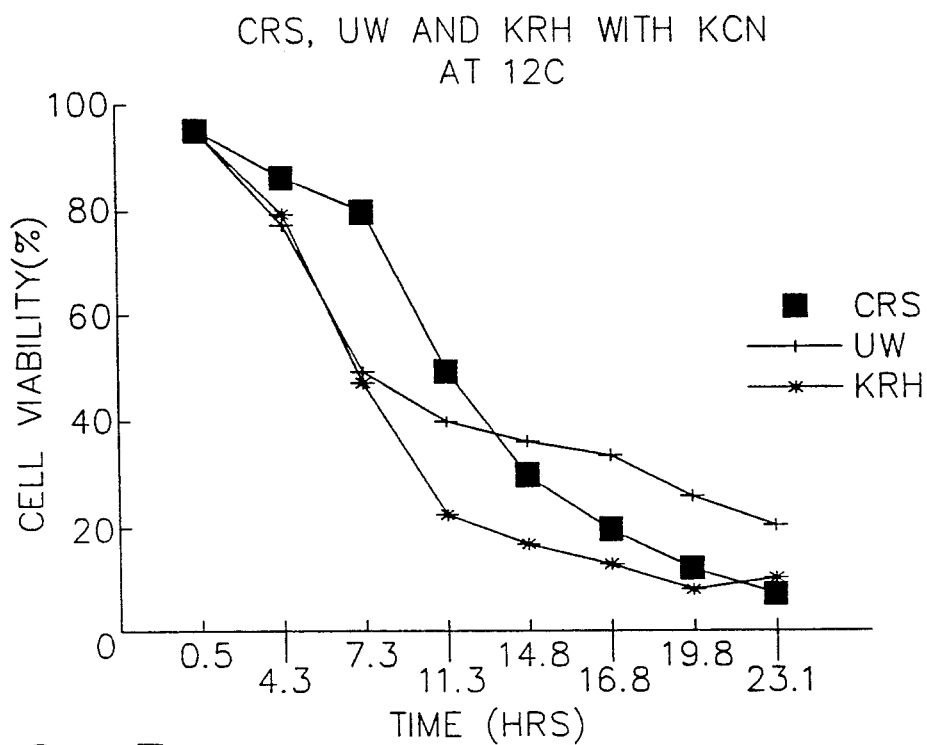
FIG. 3 shows the viability of isolated hepatocytes at 12° C. in various solutions.
Figure 4:
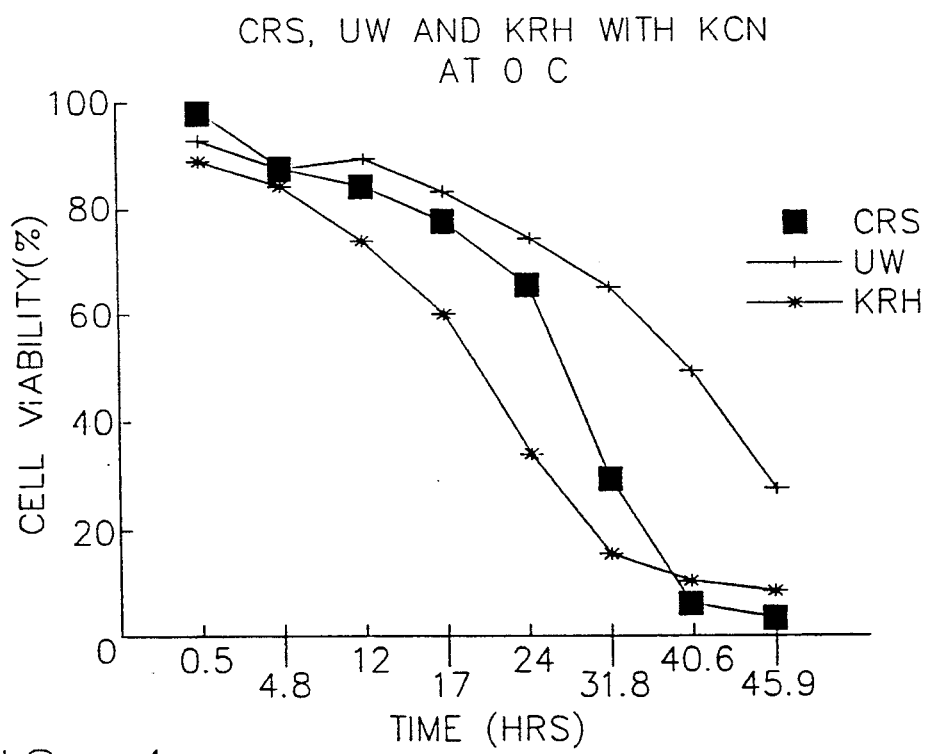
FIG. 4 shows the viability of isolated hepatocytes at 0° C. in various solutions.

Viability of Isolated Hepatocytes is Preserved in VIASPAN TM Preservation Solution and Rinse Solution as a Function of Temperature The mechanisms underlying ischemic injury and warm ischemic injury are different, since warm ischemic injury preferentially leads to parenchymal cell killing whereas cold ischemic injury preferentially makes endothelial cells susceptible to lethal reperfusion injury. Thus, the efficacy of various storage and rinse solutions may be temperature-dependent. Accordingly, we evaluated the temperature dependence of cell killing in isolated rat hepatocytes stored in either Krebs-Ringers-Hepes buffer (KRH), VIASPAN TM preservation solution (UW), or the described rinse solution (CRS). Anoxia was simulated by addition of 2.5 mM KCN, a specific inhibitor of mitochondrial respiration. At 37° C., cell killing was most rapid in Viaspan TM solution (FIG. 1). Cell killing was nearly as rapid with Krebs-Ringer's, but almost no cell killing occurred in the claimed rinse solution. Basically, an identical pattern was observed at 23° C., although overall rates of cell killing were slower (FIG. 2). At 12° C., cell killing was the same for each solution but at 0° C., the pattern reversed and cell killing was least with Viaspan TM solution (FIGS. 3 and 4). These findings indicate that the mechanisms of cell killing are different at different temperatures and that solutions which are effective at one temperature may be ineffective or harmful at another. In this regard, VIASPAN TM preservation solution was optimally effective at low temperature. At 23° C. and 37° C., the described rinse solution of the present invention was much more protective than VIASPAN TM preservation solution.

EXAMPLE 2

The Rinse Solution Protects Endothelial Cells Against Reperfusion Injury

To determine the efficacy of the described solution as a rinse in preventing lethal reperfusion injury to endothelial cells, livers of male Sprague-Dawley rats (200-300 g) were perfused via the portal vein at 3-4 ml/min/g with Krebs-Henseleit bicarbonate buffer saturated with 95% oxygen, 5% carbon dioxide in a non-recirculating system. After twenty minutes, the livers were flushed with ice-cold VIASPAN TM preservation solution for two minutes. Livers were then removed from the perfusion block, immersed in VIASPAN TM preservation solution, and placed in sealed plastic containers surrounded by ice slush (0°-1° C.). After storage intervals ranging from 24 to 96 hours, livers were perfused again with Krebs-Henseleit buffer or rinse solution at 37° C. Livers were reperfused initially at flow rates of 0.8-1.1 ml/min/g, which were gradually increased to 3-4 ml/min/g over three to five minutes. After ten minutes, buffer containing 500 μM trypan blue was infused for five more minutes, followed by fixation with 2% paraformaldehyde. Subsequently, the tissue was embedded in water-soluble glycol methacrylate, sectioned, and stained with eosin to identify the trypan blue-positive nuclei of nonviable cells.

Figure 5:
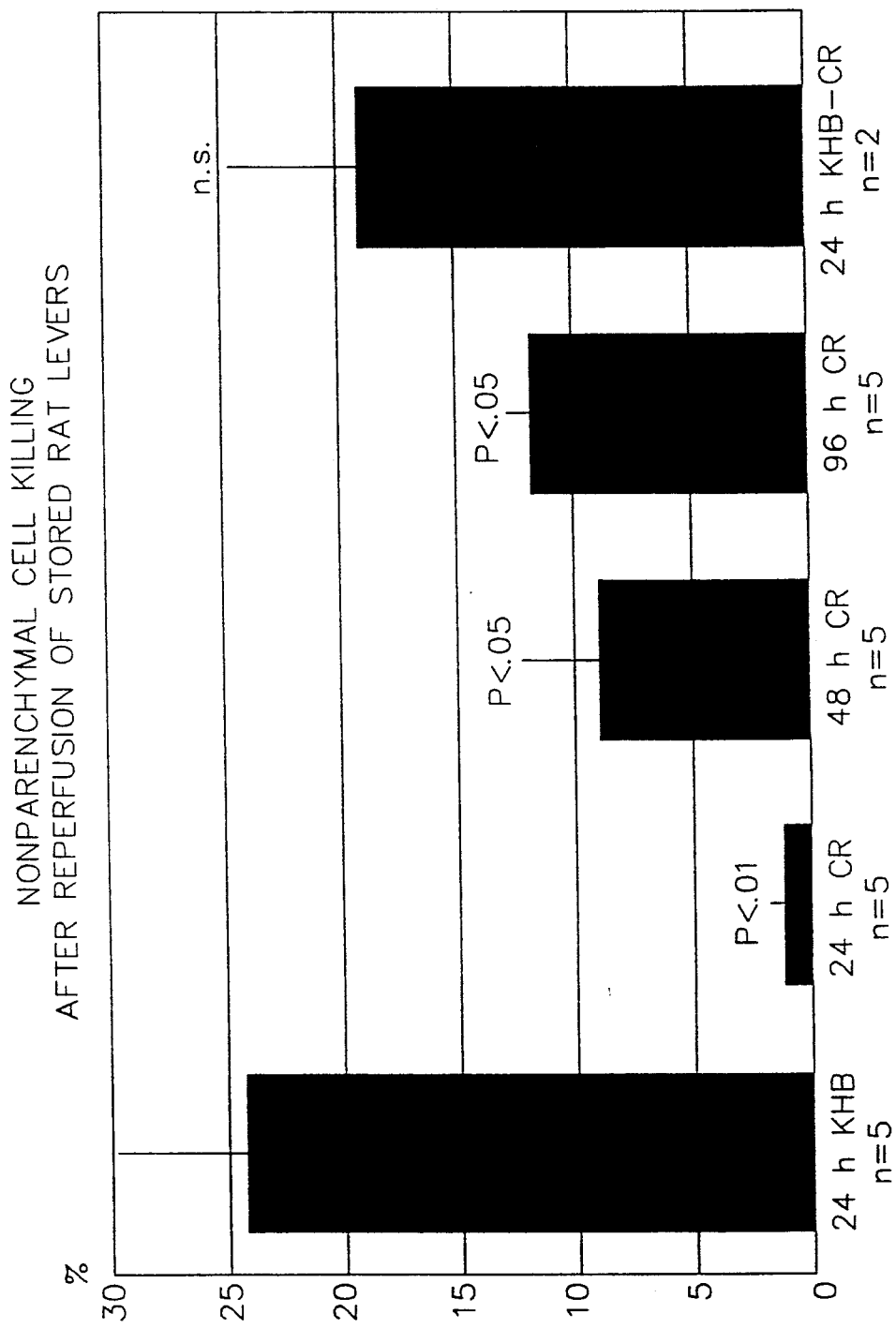
FIG. 5 shows nonparenchymal cell killing in stored livers after perfusion with various solutions.

When trypan blue uptake into nuclei was used as a criterion of loss of cell viability, marked nonparenchymal cell killing was evident in histological sections of 24 hour-stored livers after reperfusion with Krebs-Henseleit buffer. By contrast, virtually no cell killing occurred in livers reperfused with the rinse solution. Cell counts revealed that trypan blue uptake was 24.5% of all nonparenchymal cell nuclei in livers reperfused with Krebs-Henseleit versus 0.6% in livers reperfused with the rinse solution (FIG. 5). Statistically significant reduction of nonparenchymal trypan blue labeling also occurred after 48 and 96 hours of storage in livers reperfused with the rinse solution. In other experiments, 24 hour-stored livers were first reperfused with Krebs-Henseleit buffer to cause endothelial cell killing. Subsequently, these livers were infused with rinse solution and trypan blue. Under these conditions, trypan blue uptake was 19.6% (FIG. 5). Thus, the rinse solution did not interfere with trypan blue labeling of necrotic endothelial cells, and we conclude that lethal injury to endothelial cells of rat livers stored for transplantation surgery can be reduced drastically by reperfusion with the rinse solution

EXAMPLE 3

The Rinse Solution Prevents Kupffer Cell Activation

Figure 6:
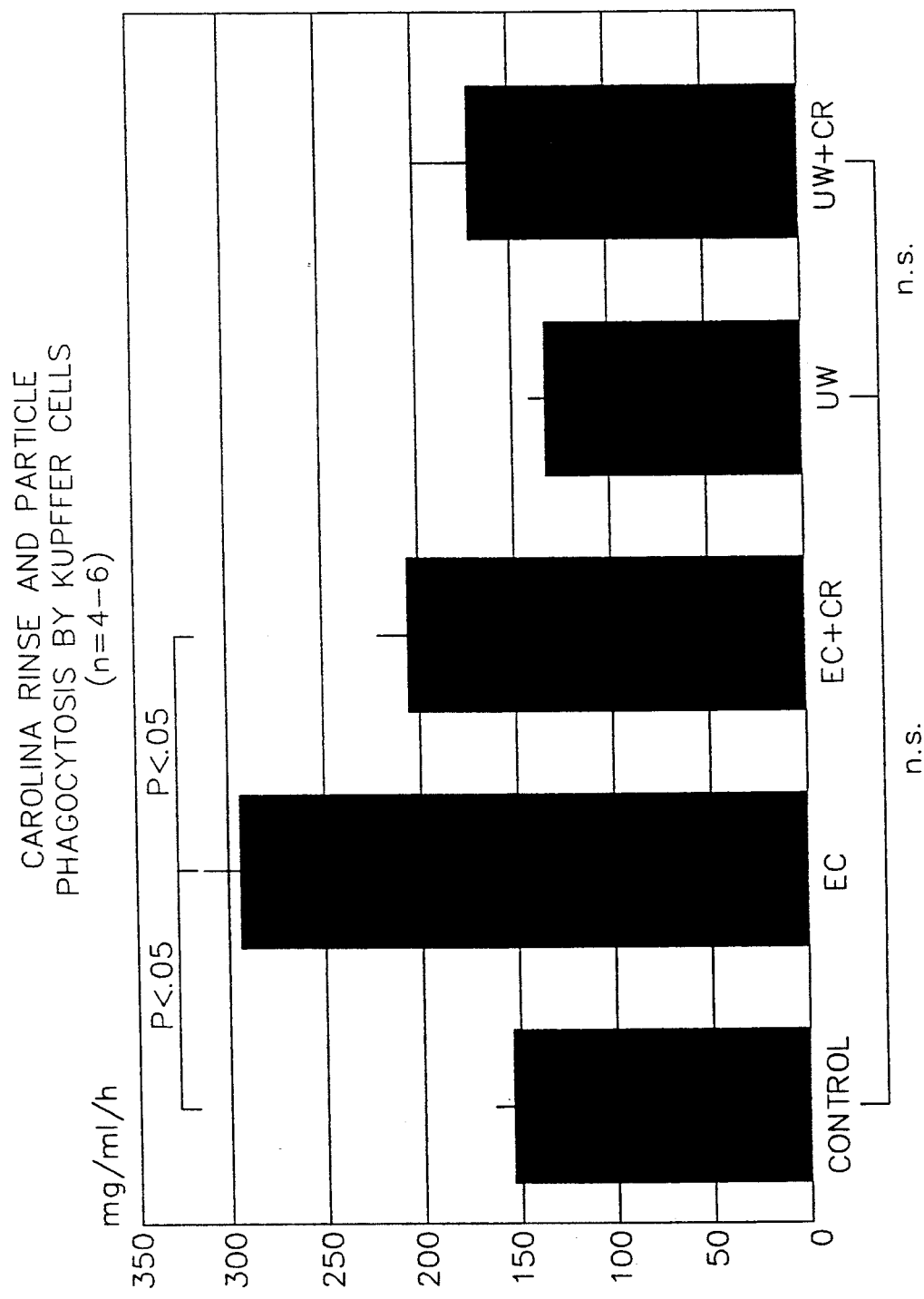
FIG. 6 compares the prevention of Kupffer cell activation after reperfusion of stored livers with various solutions.

It has been demonstrated that Kupffer cell activation occurs coincident with endothelial cell killing after reperfusion of stored livers. Since Kupffer cells in the liver account for two-thirds of all the macrophages of the body, this Kupffer cell activation may contribute substantially to the pathophysiology of graft failure after storage injury. Colloidal carbon is phagocytosed by Kupffer cells and we have developed a new method to monitor Kupffer cell activity in isolated perfused rat livers by measuring the clearance of infused colloidal carbon (K. B. Cowper, R. T. Currin, T. L. Dawson, K. A. Lindert, J. J. Lemasters and R. G. Thurman, Biochem. J. 1990, Vol. 226, p. 141-147). In control unstored livers, carbon was taken up at rates of about 150 mg/g/hr. In rat livers stored in Euro-Collins solution for 24 hours and reperfused with Krebs-Henseleit buffer as described above, a near doubling in the rate of carbon uptake occurred (FIG. 6). By contrast, if livers were reperfused with rinse solution following 24 hours storage in Euro-Collins solution, the increase of carbon uptake was significantly blunted.

EXAMPLE 4

The Described Rinse Solution Protects Against Graft Failure In Vivo After Liver Transplantation Improvement of graft survival after orthotopic liver transplantation in vivo is the ultimate criterion of efficacy of the described rinse solution. Accordingly, rat livers stored under non-surviving conditions (eight hours in Viaspan TM) were flushed with cold rinse solution and transplanted. Orthotopic transplantations were performed on inbred Lewis rats (female, 175-200 g), the use of which excluded the possibility of immunological interference. The surgical technique employed is described in detail (N. Kamada and R. Y. Calne (1979) *Transplantation* 47). Briefly, under ether anesthesia, donor livers were flushed rapidly in situ via the portal vein with 30 ml of chilled VIASPAN TM preservation solution. Cuffs were placed on the portal vein and the subhepactic vena cava, and the explanted livers were stored in VIASPAN TM preservation solution (0°-1° C.) for eight hours. During implantation, some liver grafts were rinsed with 50 ml of chilled Ringer's solution (control) or the described rinse solution by placing a cannula into the portal vein and very slowly rinsing the organ. Rinsing was performed immediately before unclamping the portal vein of the recipient rat. Implantation surgery usually required less than 50 minutes during which time the portal vein was clamped for 17 to 23 minutes. Permanent survival was defined as survival for more than thirty days after surgery. Following transplantation, blood samples were drawn for measurement of serum glutamic oxaloacetic transaminase (SGOT).

In control groups not infused with the described rinse solution (n=4) or infused with lactated Ringer's solution (n=7), liver grafts reddened slowly upon resumption of blood flow and then became dark red and spotty in pigmentation. Bile flow was not observed following implantation as is often seen with grafts which do not survive. These phenomena indicated that the microcirculation was disturbed and that damage had occurred in these grafts. The average survival time of the control groups was only about a day (FIG. 7) and SGOT values peaked to an average of 3000 units/liter one day postoperatively.

Figure 7:
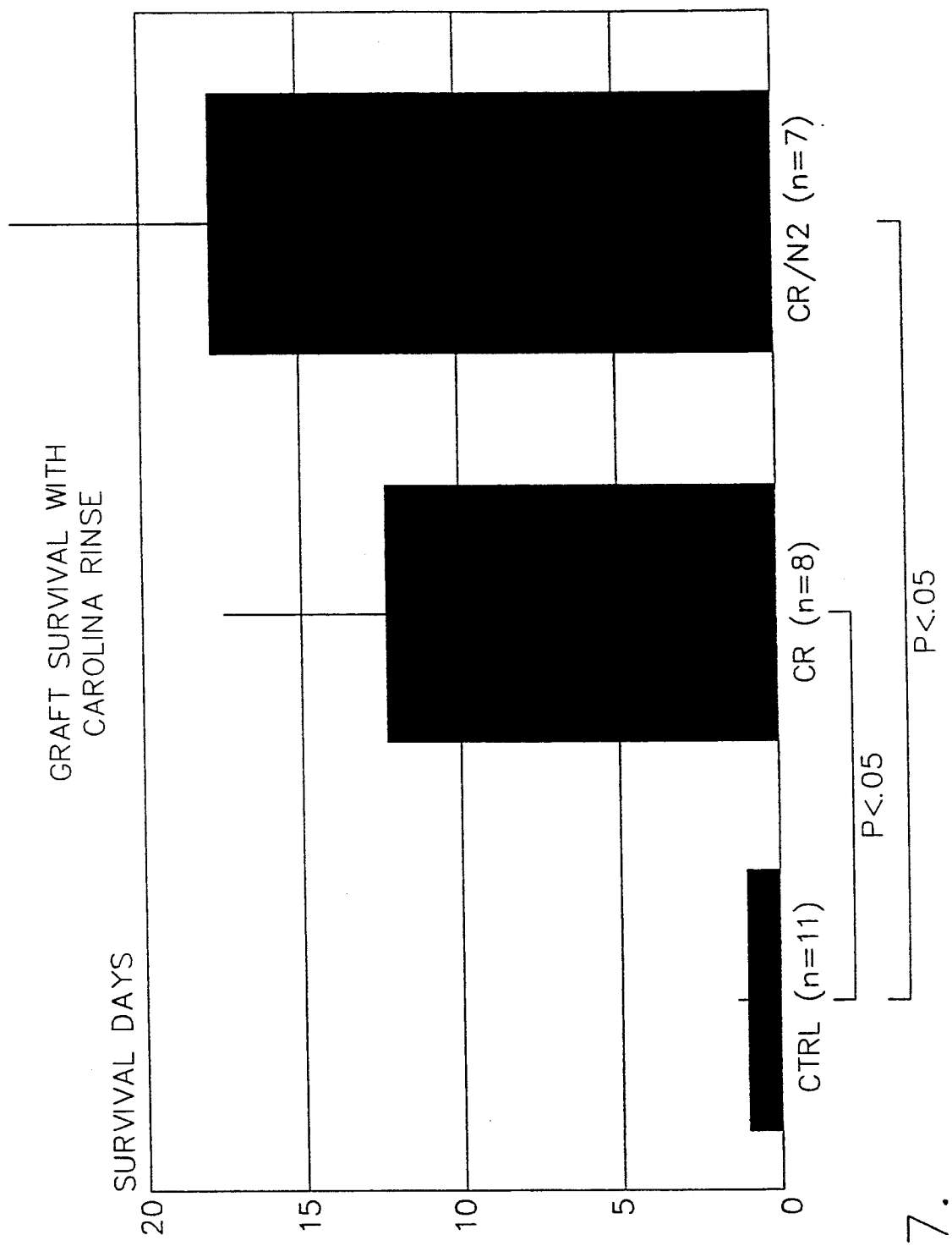
FIGS. 7 and 8 compare the protection by various solutions against graft failure in vivo after liver transplantation.
Figure 8:
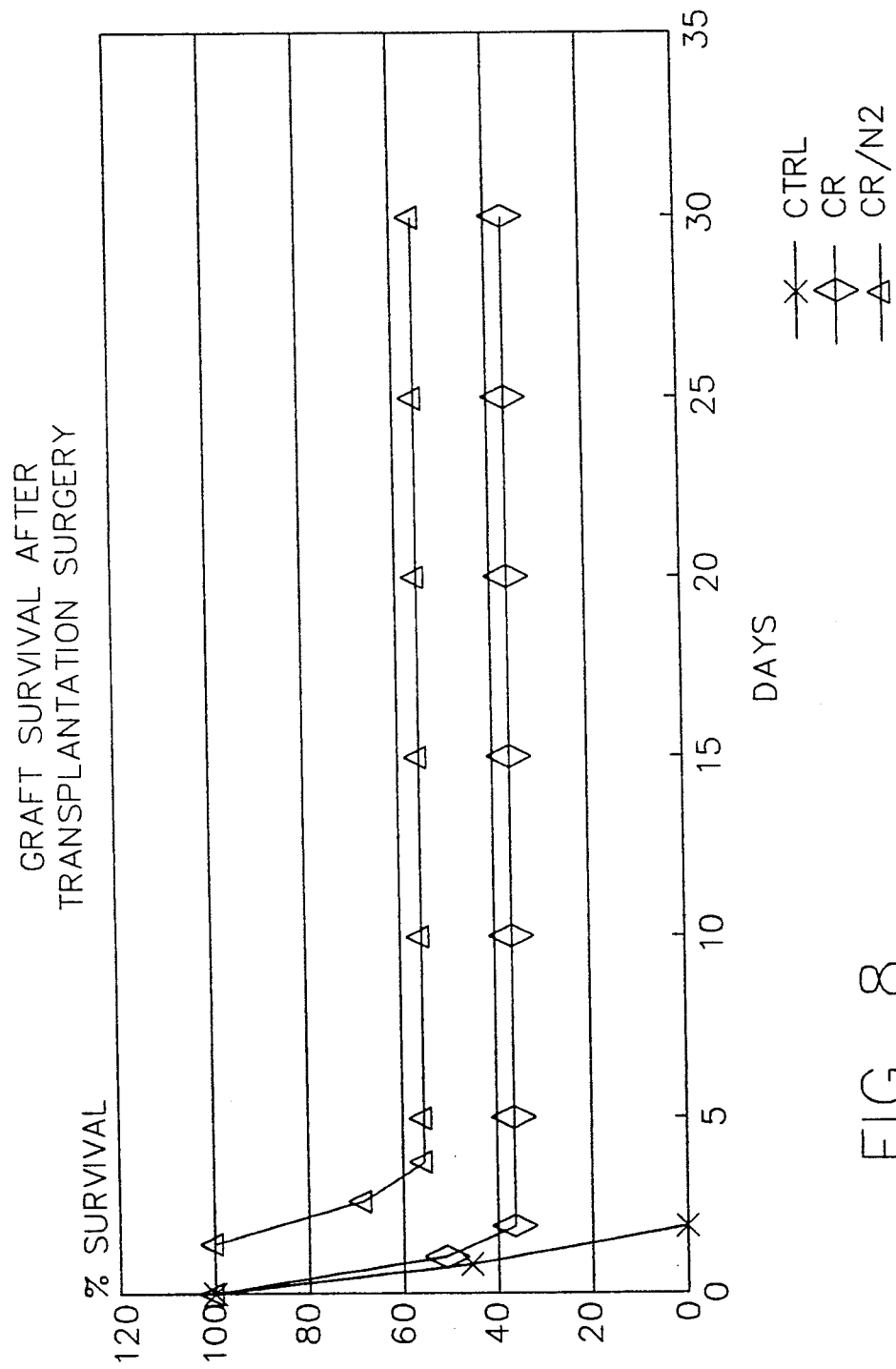
Figure 9:
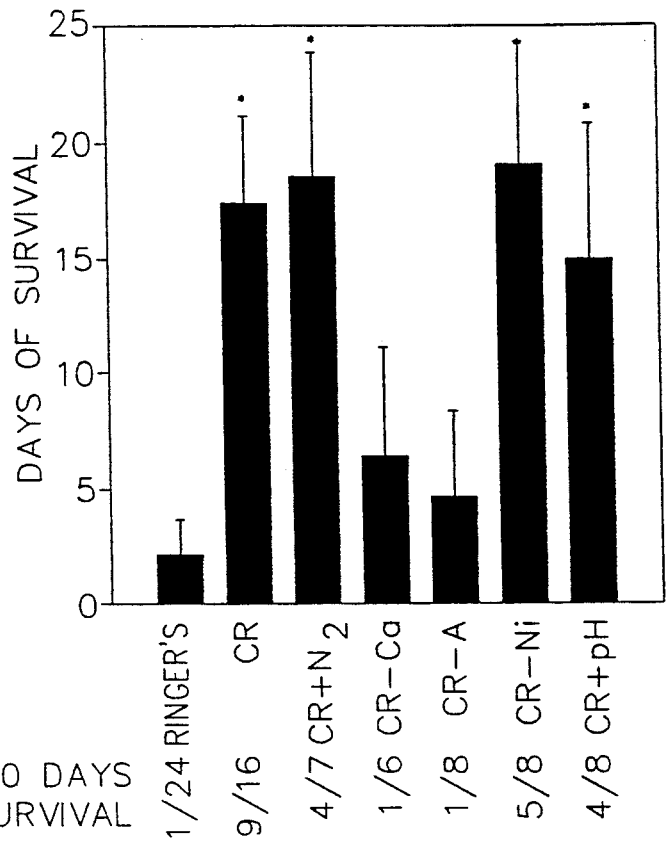
FIG. 9 shows the effect of specific components of Carolina Rinse on graft survival following orthotopic liver transplantation. Livers were rinsed and stored in UW cold storage solution at 0°-4° C. for 12 hr. Following storage, livers were rinsed with 30 ml of either Ringer's solution, Carolina Rinse, Carolina Rinse saturated with nitrogen, or Carolina Rinse with a component deleted and then implanted. Survival was assumed to be indefinite when rats were alive 30 days postoperatively. *, $p<0.05$ for comparison with control group. n=the denominator in 30-day survival figures.

In contrast, liver grafts treated with the described solution (n=8) reddened quickly upon resumption of blood flow (<1 minute). Some grafts began secreting bile within three minutes, and peak SGOT values were less than half of the control values. Significantly, the average survival time for rats receiving grafts treated with the described solution was twelve days, a nearly ten-fold increase of survival (FIG. 7). Four of eight rats survived beyond two days, and three were alive after thirty days (FIG. 8).

Some grafts were treated with $N_2$-saturated rinse solution (n=7) to investigate the possible involvement of oxygen radicals in reperfusion injury. The results from this group, including graft color, bile secretion and postoperative SGOT values, were very similar to those observed for air-saturated solution (FIGS. 7 and 8). Five of the seven rats survived beyond three days, and four were alive after thirty days. These experiments clearly demonstrate that the described rinse solution dramatically increases survival in the transplantation model.

EXAMPLE 5

Adenosine at Proper concentration in Ringer's Solution significantly Increases Liver Survival Since Carolina Rinse contains several components unique to its formula, as well as different concentrations of components found in VIASPAN TM preservation solution (UW) and Ringer's solution, the experiments described in this Example were carried out to determine which components of Carolina Rinse were most significant to improving the survivability of transplanted organs. These data indicate that adenosine, at proper concentration, is particularly important in an organ transplant rinse solution.

Transplantation

Inbred female Lewis rats (175-200 g) were used for all transplantations to exclude immunological interference. Liver transplantations were performed according to the technique described by Zimmermann and Kamada. Briefly, livers were removed and cuffs were placed on the portal vein and subhepatic vena cava of donor livers. Grafts were stored at 0°-4° C. in VIASPAN TM preservation solution (UW) for 12 hrs, then were rinsed with either 30 ml of Ringer's, VIASPAN TM preservation solution, Carolina Rinse, or Carolina Rinse saturated with nitrogen. Subsequently, livers were implanted by connecting the suprahepatic vena cava with a running suture, inserting cuffs into the appropriate vessels, and anastomosing the bile duct with an intraluminal splint. The ischemic interval due to clamping of the portal vein during the implantation procedure did not exceed 20 min. Some rats were sacrificed at 24 hrs postoperatively for histology, and survival was assumed to be indefinite when rats were alive 30 days following surgery.

Serum Enzymes

Blood samples were collected postoperatively via the tail vein at 2-day intervals during the first 7 days and at weekly intervals thereafter. Sera were separated by centrifugation and kept at −20° C. for enzyme measurements. Serum glutamic oxaloacetic transaminase (SGOT) activity was assayed using standard enzymatic procedures.

Histology

Rats were sacrificed 24 hrs postoperatively and livers were fixed with 2% paraformaldehyde:2% glutaraldehyde in Krebs-Henseleit buffer and processed for histology.

Hemoglobin Reflectance

After releasing the clamp on the portal vein, total and oxygenated hemoglobin were measured on the liver surface with a 3 channel ratio air turbine spectrophotometer. Bundles of glass optical fibers (ID 2mm) were used to direct light to the liver and to direct reflected light to wavelength ratios (660 nm/ 569 nm, 586 nm/ 577 nm, 586 nm,/ 589 nm), and total and/or oxygenated hemoglobin was calculated in accordance with known techniques.

Components of Carolina Rinse

There are a number of differences between Carolina Rinse and University of Wisconsin (UW) solution or Ringer's solution that could be responsible for its efficacy. Table 5 lists the components of Ringer's solution, Ringer's solution with adenosine, UW solution, and Carolina Rinse for comparison.

TABLE 5

Composition of Ringer's Solution, UW Solution, and Carolina Rinse

| Component | Ringer's | Ringer's + Adenosine | UW | Carolina Rinse |
|---|---|---|---|---|
| NaCl | 102 mM | 102 mM | — | 115 mM |
| KCl | 4 mM | 4 mM | — | 5 mM |
| CaCl$_2$ | 3 mM | 3 mM | — | 1.3 mM |
| KH$_2$PO$_4$ | — | — | 100 mM | 1 mM |
| MgSO$_4$ | — | — | 5 mM | 1.2 mM |
| Sodium Lactate | 28 mM | 28 mM | — | — |
| Potassium Lactobionate | — | — | 100 mM | — |
| Allpurinol | — | — | 1 mM | 1 mM |
| Desferri-oxamine | — | — | — | 1 mM |
| Glutathione | — | — | 3 mM | 3 mM |
| Nicardipine | — | — | — | 2 $\mu$M |
| Adenosine | — | 0.1 mM | 5 mM | 1 mM |
| Fructose | — | — | — | 10 mM |
| Glucose | — | — | — | 10 mM |
| Raffinose | — | — | 30 mM | — |
| Hydroxyethyl Starch | — | — | 50 g/l | 50 g/l |
| Insulin | — | — | 40 U/l | 100 U/l |
| Dexamethasone | — | — | 16 mg/l | — |
| Penicillin | — | — | 200,000 U/l | — |
| MOPS | — | — | — | 20 mM |
| pH | 7.0 | 7.0 | 7.4 | 6.5 |
| mOsm/L | 273 | 273 | 320–330 | 290–305 |

For example, while VIASPAN ™ preservation solution (UW) contains a high concentration of potassium, Carolina Rinse has extracellular inorganic ions similar to blood. Nicardipine, a dihydropyridine-type calcium channel blocker, is a component of Carolina Rinse since these calcium channel blockers have been shown to increase graft survival following transplantation. In addition, Carolina Rinse contains desferrioxamine, an iron chelator known to prevent reperfusion injury in lung, possibly by scavenging hydroxyl radicals. Fructose is included because it regenerates ATP anaerobically via glycolysis and reduces hypoxic cell death in liver. Carolina Rinse has a lower pH than either Ringer's or UW solution since a mildly acidic pH has been shown to reduce hypoxic injury to hepatocytes in vitro. Of potential importance also are the components of Carolina Rinse, such as adenosine and calcium, that occur in different concentrations than in other rinse solutions.

Effect of different components of Carolina Rinse on graft survival

Figure 15:
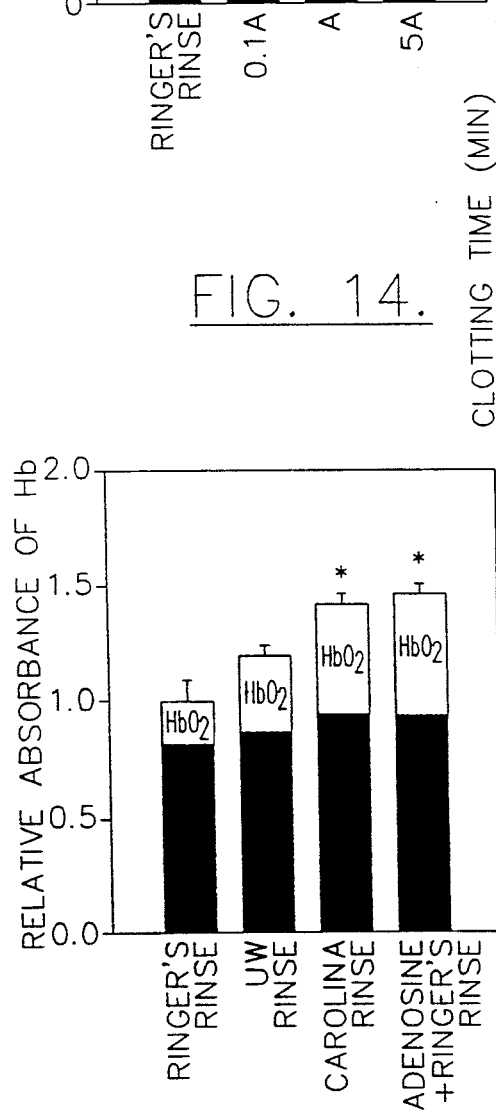
FIG. 15 shows hemoglobin reflectance in grafts rinsed with Ringer's, Ringer's with adenosine, UW or Carolina Rinse. Livers were stored and rinsed as described in the legend to FIG. 14. Entire bar represents total absorbance of hemoglobin; filled and unfilled portions of the bar represent deoxygenated and oxygenated fractions, respectively. Hb, hemoglobin; *, $p<0.05$ for comparison with Ringer's group. n=6-8 per group.

To determine which component(s) of Carolina Rinse accounts for its efficacy, grafts were rinsed with 30 ml of variations of Carolina Rinse prior to completion of implantation. Rinsing with Carolina Rinse or Carolina Rinse saturated with nitrogen significantly increased the average length of survival from less than one day in controls rinsed with Ringer's solution to 17 and 18 days, respectively (FIG. 15). Further, while only 1 out of 24 grafts survived 30 days postoperatively (considered permanent in these studies) in the control group, 9 of 16 in the Carolina Rinse group and 4 of 7 in the Carolina Rinse plus nitrogen group lived indefinitely (FIG. 15). Deleting nicardipine from Carolina Rinse did not alter its beneficial effects; grafts in this group lived an average of 18 days and 5 out of 8 were alive 30 days postoperatively (FIG. 15). Similarly, raising the pH to 7.0 did not significantly change the effects of Carolina Rinse, with grafts surviving an average of 15 days and 4 out of 8 living indefinitely (FIG. 15). In contrast, subtracting calcium or adenosine from Carolina Rinse dramatically reduced survival. Rinsing with Carolina Rinse without calcium significantly decreased average survival time to about 6 days, and only 1 of 6 grafts lived 30 days postoperatively (FIG. 15). In addition, deleting adenosine reduced the average length of survival to approximately 5 days, with 1 of 8 grafts surviving indefinitely (FIG. 15).

Graft survival following rinsing with Ringer's solution plus adenosine

Figure 10:
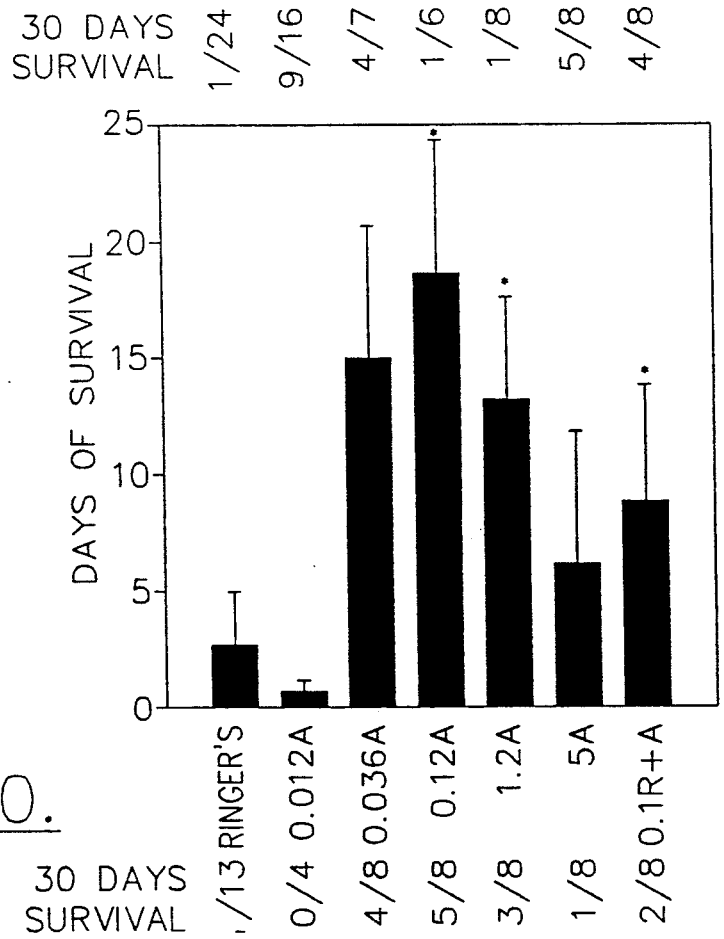
FIG. 10 shows the effect of different concentrations of adenosine on graft survival following orthotopic liver transplantation. Livers were stored as described in the legend to FIG. 9, and grafts were rinsed with Ringer's solution containing 0, 0.012, 0.036, 0.12, 1.2, or 5.0 mM adenosine or 0.1 mM ribose plus 0.1 mM adenine. *, $p<0.05$ for comparison with Ringer's group. n=denominator in 30-day survival figures.

Adenosine was added to Ringer's solution at varying concentrations to determine whether a specific concentration is key to increasing graft survival. In the control group rinsed with Ringer's alone, average graft survival was about two days, and only 1 of 13 grafts lived 30 days postoperatively (FIG. 10). No improvement was shown with the addition of 0.012 mM adenosine to Ringer's solution. However, greater concentrations of adenosine increased survival time, with the best results obtained with 0.12 mM adenosine. In this group, the average length of survival was almost 20 days, and 5 of 8 grafts survived indefinitely, results similar to those obtained with Carolina Rinse. Concentrations of 0.036, 1.2, and 5 mM adenosine in Ringer's solution resulted in survival times of approximately 15, 13, and 6 days and survival rates of 4 of 8, 3 of 8, and 1 of 8 grafts, respectively. In addition, one group was rinsed with Ringer's solution containing ribose (0.1 mM) and adenine (0.1 mM), which like adenosine provide energy but unlike adenosine do not inhibit platelet aggregation. In this group, the average length of survival was about 9 days and 2 of 8 grafts survived 30 days postoperatively (FIG. 10).

Figure 11:
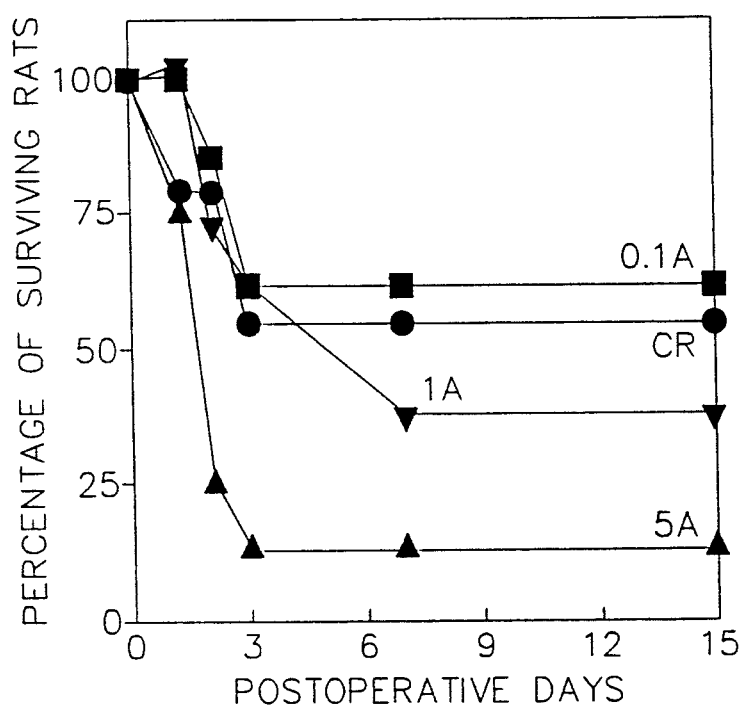
FIG. 11 shows the percentage of surviving rats 0-15 days postoperatively following rinsing with Carolina Rinse or Ringer's solution containing adenosine. Livers were stored as in FIG. 9, and grafts were rinsed with Carolina Rinse or Ringer's rinse containing 0.1, 1.0, or 5.0 adenosine indicated. n=at least 4 per group.

Ringer's Rinse with 0.1 mM adenosine and Carolina Rinse also had similar effects on early graft survival (FIG. 11). One day postoperatively, 100% and 80% of rats in the Ringer's plus 0.1 mM adenosine and Carolina Rinse groups survived, respectively, and by day 3 the survival rate had fallen to around 60% in both groups and remained at that level through day 15 (FIG. 11). In the Ringer's with 1.0 mM adenosine group, 100% of rats were alive one day postoperatively, but the percentage fell sharply until it stabilized at around 40% on day 6 (FIG. 11). Poorest survival rates were found in the group rinsed with Ringer's containing 5.0 mM adenosine, the concentration in Viaspan ™, with 75% of rats surviving through the first day and only 10% surviving by day 3 (FIG. 11).

SGOT activity following transplantation

Figure 12A:
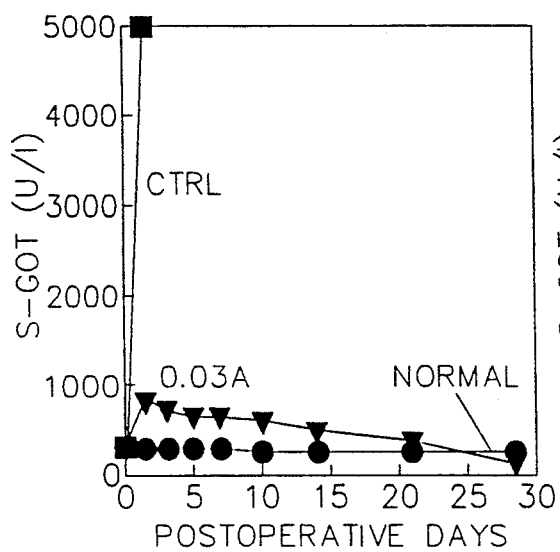
FIG. 12 shows the effect of different concentrations of adenosine on SGOT activity following orthotopic liver transplantation. Livers were stored as in FIG. 9 and grafts were rinsed with Ringer's solution containing 0.036 mM adenosine (12A), 0.12 mM adenosine (12B), 1.2 mM adenosine (12C);, or 5.0 mM adenosine (12D). Blood samples were collected postoperatively via the tail vein of recipient rats at 2-day intervals during the first week and at weekly intervals thereafter.
Figure 12B:
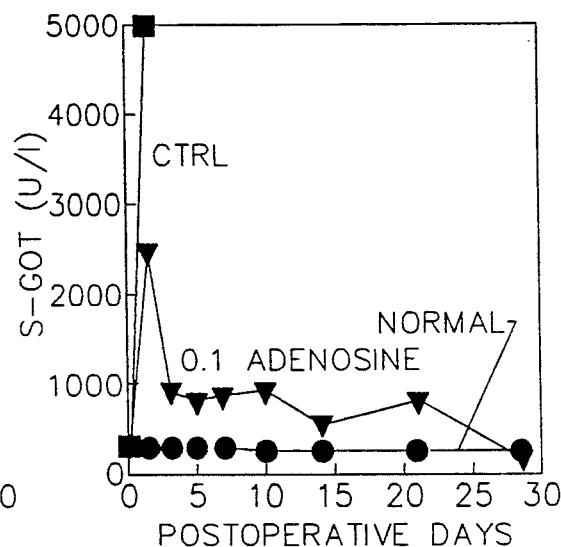
Figure 12C:
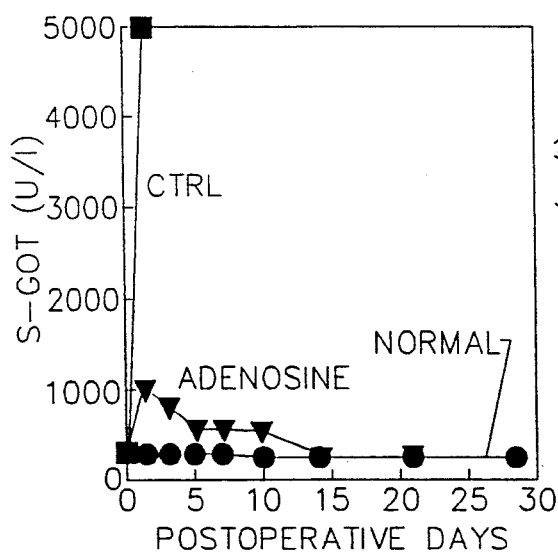
Figure 12D:
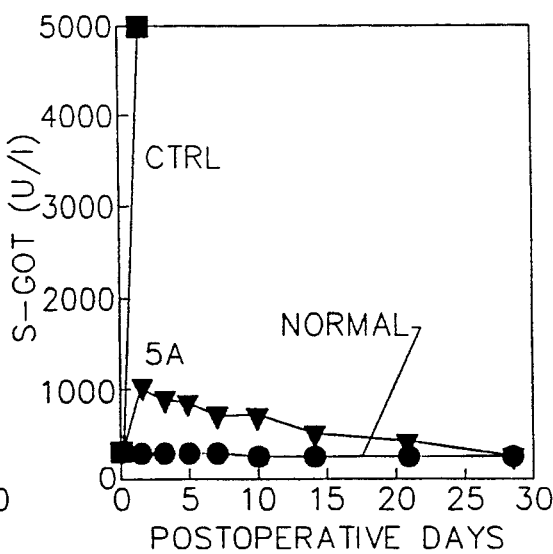

Liver damage following transplantation surgery was evaluated by measuring SGOT activity. FIG. 12 depicts SGOT activity up to 30 days postoperatively in livers rinsed with Ringer's solution containing 0.03, 0.1, 1.0 or 5.0 mM adenosine. In control experiments, SGOT activity peaked at 5000 U/l during the first day, while in groups rinsed with 0.03, 1.0, or 5.0 mM adenosine, enzyme release peaked at approximately 1000 U/l the day following surgery with a subsequent steady decline to normal values of about 250 U/l (FIG. 12A,C,D). Interestingly, although 0.1 mM adenosine was the most effective concentration for extending survival, in this group SGOT activity reached about 2500 U/l following surgery, fell to 1000 around day 3, and fluctuated at levels above normal 21 days postoperatively, when levels began to show a steady decline (FIG. 12B). However, by including at least one antioxidant, enzyme release can be virtually abolished.

Effect of adenosine on index of liver damage

Figure 13:
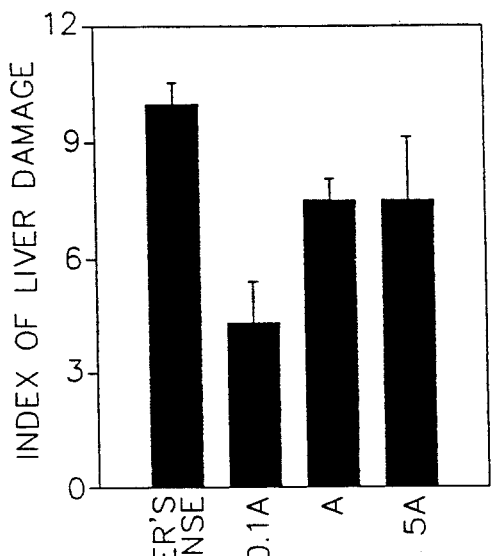
FIG. 13 shows the effect of adenosine on index of liver damage. Livers were stored as described in the legend to FIG. 9, and grafts were rinsed with Ringer's solution or Ringer's containing 0.12, 1.2, or 5 mM adenosine. Liver damage was scored using a scale of 0-5 based on the degree of necrosis and 0-2 based on six structural parameters: cellular swelling, acidophilic nuclear inclusions, nuclear pyknosis, cellular deposition, cytoplasmic vacuolization and sinusoidal vacuoidal dilation. *, $p<0.05$ for comparison with Ringer's rinse group.

Grafts rinsed with Ringer's solution after 12 hr of storage in VIASPAN ™ preservation solution were scored for liver damage as described in the legend to FIG. 13. In the Ringer's Rinse group, the index of liver damage was around 10, and adding 1 or 5 mM adenosine slightly reduced the level of damage to about 7.5 (FIG. 13). Grafts rinsed with Ringer's with 0.1 mM adenosine, however, scored 4, a significant reduction in damage compared to the control group (FIG. 13).

Effect of rinse solutions on postoperative clotting time

Figure 14:
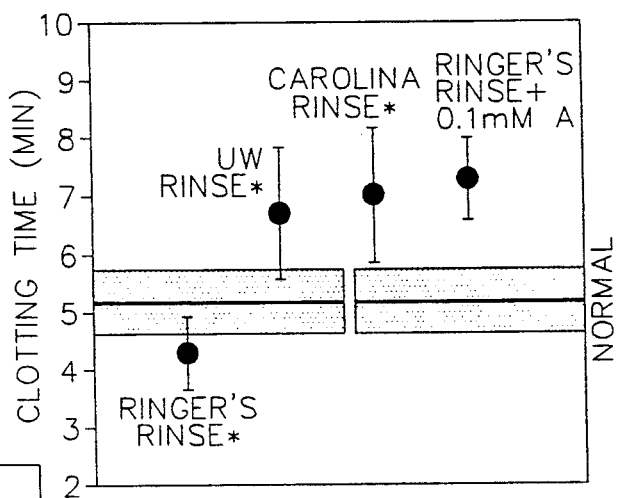
FIG. 14 shows the effect of rinse solutions on postoperative clotting time. Livers were stored as in FIG. 9, and grafts were rinsed with Ringer's, Ringer's with 0.1 mM adenosine, UW, or Carolina Rinse. Blood samples were collected from the subhepatic vena cava after the clamp on the portal vein was released, and clotting time was calculated. *, $p<0.05$ for comparison with normal group.

Following transplantation of livers stored in VIASPAN ™ preservation solution and rinsed with Ringer's solution or Carolina Rinse, blood samples were taken and clotting time determined. In the control group rinsed with Ringer's solution, clotting time was reduced from normal times of 5.2 minutes to approximately 4.5 minutes (FIG. 14). In contrast, rinsing with Carolina Rinse or with Ringer's containing 0.1 mM adenosine both increased clotting times to approximately 7 minutes, and rinsing with Ringer's solution containing ribose and adenine further elevated the clotting time to 7.3 minutes (FIG. 14).

Oxygenation of hemoglobin following transplantation

Total hemoglobin and the oxygenated fraction were measured to evaluate hepatic microcirculation in transplanted livers stored in VIASPAN ™ preservation solution and rinsed with either Ringer's, VIASPAN ™ preservation solution, Carolina Rinse, or Ringer's with adenosine (0.12 mM). In the Ringer's rinse group, total relative absorbance of hemoglobin was approximately 1.0, and less than 20% of the total was oxygenated (FIG. 15). In the VIASPAN ™ preservation solution rinse group, the amount of total hemoglobin increased slightly, and a larger fraction of the total, about 33%, was oxygenated (FIG. 15). Both the Carolina Rinse and Ringer's with adenosine groups showed a significant increase in hemoglobin absorbance, indicating a significant improvement in microcirculation. In both groups, total hemoglobin absorbance was about 1.5, and about 35% of the total was oxygenated (FIG. 15).

The present invention has been described in detail and with particular reference to the preferred embodiments. Those skilled in the art will appreciate that changes can be made without departing from the spirit and scope thereof. Accordingly, the present invention is to be defined by the following claims, with equivalents of the claims to be included therein.

That which is claimed is:

1. A solution for the preservation and storage of organs and tissues, at temperatures of 0° C. to 37° C. intended for implantation in a patient requiring such implantation, and for rinsing other preservation and storage solution from an organ prior to implantation, said solution comprising, in one liter of solution:
from about 0.12 to about 1.2 mM adenosine; sodium, potassium, calcium and magnesium ions in a physiologically acceptable amount; and water for injection sufficient to make a liter of solution; said solution having a pH of about 6.0 to 7.5, and a concentration of potassium of less than 6 MEQ/L.

2. The solution of claim 1 being substantially free of oxygen.

3. A solution according to claim 1, further comprising about 5% by weight of hydroxyethyl starch, said hydroxyethyl starch having a weight average molecular weight of from about 50,000 to about 1,000,000 daltons, a degree of substitution of from about 0.4 to about 0.7, and being substantially free of contaminants, including ethylene glycol, ethylene chlorohydrin, acetone and sodium chloride.

4. A solution for the rinsing of organs intended for implantation in a patient requiring such implantation prior to implantation and for the storage of such organs, said solution comprising:

| | | | |
|---|---|---|---|
| NaCl | 85 | to | 145 mM |
| KCl | 3 | to | 6 mM |
| CaCl$_2$ | 1.0 | to | 1.6 mM |
| KH$_2$PO$_4$ | 0.7 | to | 1.3 mM |
| Adenosine | 0.12 | to | 1.2 mM |
| Distilled deionized water | | q.s. | | and said solution having a pH of 6.0 to 7.4.

5. A method for rinsing preservation or storage solution from organs or tissue intended for implantation in a patient requiring such implantation, said method comprising:
rinsing said organ or tissue prior to implantation with a solution comprising in one liter of solution:
from about 0.12 to 1.2 mM adenosine; sodium, potassium, calcium and magnesium ions in a physiologically acceptable amount; and water for injection sufficient to make a liter of solution; said solution having a pH of about 6.0 to 7.5, and a concentration of potassium of less than 6 MEQ/L.

6. A method for the preservation and storage at from about 12° C. to about 37° C. of organs or tissue intended for implantation in a patient requiring such implantation, said method comprising:
contacting said organ or tissue with a solution comprising, in one liter of solution:
from about 0.12 to 1.2 mM adenosine; sodium, potassium, calcium and magnesium ions in a physiologically acceptable amount; and water for injection sufficient to make a liter of solution; said solution having a pH of about 6.0 to 7.5, and a concentration of potassium of less than 6 MEQ/L.

7. A solution according to claim 1 having a pH of 6.5.

8. A solution according to claim 1, further comprising from 0.05 to 5.0 mM allopurinol.

9. A solution according to claim 1, further comprising 0.5 to 10 mM glutathione.

10. A solution according to claim 1, further comprising 0.1 to 5.0 mM nicardipine.

11. A solution according to claim 1, further comprising 0.02 to 2.0 mM desferrioxamine.

12. A solution according to claim 4 being substantially free of oxygen.

13. A solution according to claim 4, having a pH of 6.5.

14. A solution according to claim 4, further comprising from 0.05 to 5.0 mM allopurinol.

15. A solution according to claim 4, further comprising 0.5 to 10 mM glutathione.

16. A solution according to claim 4, further comprising 0.1 to 5.0 mM nicardipine.

17. A solution according to claim 4, further comprising 0.02 to 2.0 mM desferrioxamine.

18. A method according to claim 5, said solution comprising:

| | | | |
|---|---|---|---|
| NaCl | 85 | to | 145 mM |
| KCl | 3 | to | 6 mM |
| CaCl$_2$ | 1.0 | to | 1.6 mM |
| KH$_2$PO$_4$ | 0.7 | to | 1.3 mM |
| Adenosine | 0.12 | to | 1.2 mM |
| Distilled deionized water | | q.s. | | and said solution having a pH of 6.0 to 7.4.

19. A solution according to claim 5, said solution being substantially free of oxygen.

20. A solution according to claim 5, said solution having a pH of 6.5.

21. A solution according to claim 5, said solution further comprising from 0.05 to 5.0 mM allopurinol.

22. A solution according to claim 5, said solution further comprising 0.5 to 10 mM glutathione.

23. A solution according to claim 5, said solution further comprising 0.1 to 5.0 mM nicardipine.

24. A solution according to claim 5, said solution further comprising 0.02 to 2.0 mM desferrioxamine.

25. A method according to claim 5, said solution comprising:

| | | | |
|---|---|---|---|
| NaCl | 85 | to | 145 mM |
| KCl | 3 | to | 6 mM |
| CaCl$_2$ | 1.0 | to | 1.6 mM |
| KH$_2$PO$_4$ | 0.7 | to | 1.3 mM |
| Adenosine | 0.12 | to | 1.2 mM |
| Distilled deionized water | | q.s. | | and said solution having a pH of 6.0 to 7.4.

26. A method according to claim 6, said solution being substantially free of oxygen.

27. A solution according to claim 6, said solution having a pH of 6.5.

28. A solution according to claim 6, said solution further comprising from 0.05 to 5.0 mM allopurinol.

29. A solution according to claim 6, said solution further comprising 0.5 to 10 mM glutathione.

30. A solution according to claim 6, said solution further comprising 0.1 to 5.0 mM nicardipine.

31. A solution according to claim 6, said solution further comprising 0.02 to 2.0 mM desferrioxamine.

* * * * *

UNITED STATES PATENT AND TRADEMARK OFFICE
CERTIFICATE OF CORRECTION

PATENT NO. : 5,145,771
DATED : 3 February 1992
INVENTOR(S) : John J. Lemasters and Ronald G. Thurman It is certified that error appears in the above-identified patent and that said Letters Patent is hereby corrected as shown below:

Column 1, Line 37, after VIASPAN ™ please add, --preservation solution--.

Column 1, Line 63, after VIASPAN ™ please add, --preservation--.

Column 2, Line 17, correct "MoCord" to read --McCord--.

Column 2, Line 25, after *Hepatology* please add --5--.

Column 2, Line 48, after FASEB J. please add --3--.

Column 7, Line 32, after limiting please add --the scope--.

Column 9, Line 22, after *Transplantation* please add --28--.

Column 16, Lines 21, 23, 25, 27 and 29, please correct "solution" to read --method--.

Signed and Sealed this

Seventh Day of September, 1993

Attest:

*Attesting Officer*

BRUCE LEHMAN

*Commissioner of Patents and Trademarks*